US00PP25873P2

(12) United States Plant Patent
Lannes

(10) Patent No.: US PP25,873 P2
(45) Date of Patent: Sep. 8, 2015

(54) ***MANDEVILLA* PLANT NAMED 'LANLOUISIANA'**

(50) Latin Name: *Mandevilla hybrida*
Varietal Denomination: Lanlouisiana

(71) Applicant: Robert Lannes, Malause (FR)

(72) Inventor: Robert Lannes, Malause (FR)

(73) Assignee: D. H. M. Innovations S.A.S., Malause (FR)

( * ) Notice: Subject to any disclaimer, the term of this patent is extended or adjusted under 35 U.S.C. 154(b) by 78 days.

(21) Appl. No.: 13/998,555

(22) Filed: Nov. 8, 2013

(51) Int. Cl.
*A01H 5/02* (2006.01)

(52) U.S. Cl.
USPC ..... Plt./232

(58) Field of Classification Search
USPC ..... Plt./232
CPC ..... A01H 5/02; A01H 5/00
See application file for complete search history.

*Primary Examiner* — Kent L Bell
(74) *Attorney, Agent, or Firm* — C. A. Whealy

(57) ABSTRACT

A new and distinct cultivar of *Mandevilla* plant named 'Lanlouisiana', characterized by its upright and vining plant habit; moderately vigorous to vigorous growth habit; relatively long internodes; large glossy dark green-colored leaves; freely flowering habit; and large scarlet red-colored flowers.

2 Drawing Sheets

Botanical designation: *Mandevilla hybrida.*
Cultivar denomination: 'LANLOUISIANA'.

BACKGROUND OF THE INVENTION

The present invention relates to a new and distinct cultivar of *Mandevilla* plant, botanically known as *Mandevilla hybrida* and hereinafter referred to by the name 'Lanlouisiana'.

The new *Mandevilla* plant is a product of a planned breeding program conducted by the Inventor in Malause, France. The objective of the breeding program is to create new vining-type *Mandevilla* plants with numerous attractive flowers.

The new *Mandevilla* plant originated from a cross-pollination conducted by the Inventor in Malause, France in June, 2009 of a proprietary selection of *Mandevilla hybrida* identified as code number 05-040-07, not patented, as the female, or seed parent with *Mandevilla hybrida* 'Sunmandecrikin', disclosed in U.S. Plant Pat. No. 17,736, as the male, or pollen, parent. The new *Mandevilla* plant was discovered and selected by the Inventor as a single flowering plant from within the progeny of the stated cross-pollination in a controlled greenhouse environment in Malause, France in June, 2012.

Asexual reproduction of the new *Mandevilla* plant by cuttings in a controlled greenhouse environment in Malause, France, since December, 2012 has shown that the unique features of this new *Mandevilla* plant are stable and reproduced true to type in successive generations.

SUMMARY OF THE INVENTION

Plants of the new *Mandevilla* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Lanlouisiana'.

These characteristics in combination distinguish 'Lanlouisiana' as a new and distinct *Mandevilla* plant:

1. Upright and vining plant habit.
2. Moderately vigorous to vigorous growth habit.
3. Relatively long internodes.
4. Large glossy dark green-colored leaves.
5. Freely flowering habit.
6. Large scarlet red-colored flowers.

Plants of the new *Mandevilla* can be compared to plants of the female parent selection. Plants of the new *Mandevilla* differ primarily from plants of the female parent selection in the following characteristics:

1. Plants of the new *Mandevilla* have longer internodes than plants of the female parent selection.
2. Plants of the new *Mandevilla* and the female parent selection differ in flower color as plants of the female parent selection have pink-colored flowers.

Plants of the new *Mandevilla* can be compared to plants of the male parent, 'Sunmandecrikin'. Plants of the new *Mandevilla* differ primarily from plants of 'Sunmandecrikin' in the following characteristics:

1. Plants of the new *Mandevilla* are more vigorous than plants of 'Sunmandecrikin'.
2. Plants of the new *Mandevilla* have longer internodes than plants of 'Sunmandecrikin'.
3. Plants of the new *Mandevilla* flower earlier than plants of 'Sunmandecrikin'.
4. Plants of the new *Mandevilla* and 'Sunmandecrikin' differ slightly in flower color.

Plants of the new *Mandevilla* can also be compared to plants of *Mandevilla hybrida* 'Lanarizona', disclosed in U.S. Plant Pat. No. 23,672. In side-by-side comparisons conducted in Malause, France, plants of the new *Mandevilla* differed primarily from plants of 'Lanarizona' in flower color as plants of 'Lanarizona' have white-colored flowers. In addition, plants of the new *Mandevilla* had smoother leaves than plants of 'Lanarizona'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Lanlouisiana' grown in a container.

The photograph on the second sheet is a close-up view of a typical flower of 'Lanlouisiana'.

DETAILED BOTANICAL DESCRIPTION

The aforementioned photographs and following observations, measurements and values describe plants grown during the spring in 21-cm containers in polyethylene-covered greenhouse in Malause, France and under cultural practices typical of *Mandevilla* commercial production. During the production of the plants, day temperatures ranged from 15° C. to 26° C. and night temperatures ranged from 14° C. to 15° C. Plants were six months old when the photographs and description were taken. In the following description, color references are made to The Royal Horticultural Society Colour Chart, 2007 Edition, except where general terms of ordinary dictionary significance are used.

Botanical classification: *Mandevilla hybrida* 'Lanlouisiana'.

Parentage:

*Female, or seed, parent*.—Proprietary selection of *Mandevilla hybrida* identified as code number 05-040-07.

*Male, or pollen, parent*.—*Mandevilla hybrida* 'Sunmandecrikin', disclosed in U.S. Plant Pat. No. 17,736.

Propagation:

*Type*.—By vegetative cuttings.

*Time to initiate roots, summer*.—About two weeks at 23° C. to 30° C.

*Time to initiate roots, winter*.—About three weeks at 23° C. to 25° C.

*Time to produce a rooted young plant, summer*.—About five to six weeks at 23° C. to 30° C.

*Time to produce a rooted young plant, winter*.—About six to eight weeks at 23° C. to 25° C.

*Root description*.—Fibrous, fine; light yellowish white in color.

*Rooting habit*.—Freely branching; medium density.

Plant description:

*Plant and growth habit*.—Upright and vining plant habit; twining upright; moderately vigorous to vigorous growth habit.

*Plant height*.—About 70.5 cm.

*Plant diameter (spread)*.—About 43 cm.

*Lateral branch description*.—Branching habit: Freely branching habit with about seven lateral branches developing per plant; pinching enhances lateral branch development. Length: About 125 cm. Diameter: About 4 mm. Internode length: Relatively long, about 12.4 cm. Strength: Strong. Texture: Smooth, glabrous; luster, moderately glossy. Color, developing: Close to 146B to 146C; exposed to sunlight, becoming closer to 176A. Color, developed: Close to between 199B and 200D.

Leaf description:

*Arrangement*.—Opposite, simple.

*Length*.—About 10.3 cm.

*Width*.—About 6.8 cm.

*Shape*.—Oblong to ovate and elliptic.

*Apex*.—Abruptly acute.

*Base*.—Truncate.

*Margin*.—Entire.

*Texture, upper and lower surfaces*.—Smooth, glabrous; luster, glossy.

*Venation pattern*.—Pinnate, reticulate.

*Color*.—Developing leaves, upper surface: Close to between 141A and 143A. Developing leaves, lower surface: Close to between 143A and 146A. Full expanded leaves, upper surface: Close to between N137A and 147A; venation, close to 143B. Fully expanded leaves, lower surface: Close to between 146B and 147B; venation, close to 174D.

*Petiole length*.—About 1.7 cm.

*Petiole diameter*.—About 3 mm.

*Petiole texture, upper and lower surfaces*.—Smooth, glabrous.

*Petiole color, upper surface*.—Close to 143C.

*Petiole color, lower surface*.—Close to 143C slightly tinged with close to 174D.

Flower description:

*Flower type and flowering habit*.—Single salverform flowers arranged in axillary cymes; flowers star-shaped and face mostly upright and outwardly; freely flowering habit with about ten flowers developing per inflorescence and about 140 flowers developing per plant.

*Natural flowering season*.—Plants flower continuously from early summer into the autumn in France.

*Flower longevity on the plant*.—About seven days; flowers not persistent.

*Fragrance*.—None detected.

*Inflorescence height*.—About 18.9 cm.

*Inflorescence diameter*.—About 14.1 cm.

*Flower buds*.—Length: About 6.3 cm. Diameter: About 1.1 cm. Shape: Narrowly obovate. Color: Close to 145B; towards the base, close to 145A; towards the apex, close to 53B to 53C.

*Flowers*.—Appearance: Flared trumpet, corolla fused and five-parted. Diameter: About 8.5 cm. Depth (length): About 5.5 cm. Tube length: About 5 cm.

*Corolla*.—Quantity and arrangement: Five petals arranged in a single whorl and fused toward the base. Petal length: About 9.5 cm. Petal width: About 4.2 cm. Petal shape and appearance: Roughly spatulate; lower 52.5% of the petal is fused. Petal apex: Rounded. Petal margin: Entire. Petal texture, upper surface: Smooth, glabrous; velvety. Petal texture, lower surface: Smooth, glabrous; luster, slightly glossy. Throat and tube texture: Smooth, glabrous. Color: Petal, when opening, upper surface: Close to 46B; towards the apex, close to 53A; throat, distally, darker than 53A; throat, close to 31A; at the base of the throat, close to 145A. Petal, when opening, lower surface: Close to 47B; towards the apex, close to 53B; tube, close to 51B; at the base of the tube, close to N144C. Petal, fully opened, upper surface: Close to between 46B and 53A; color does not change with development; throat, distally, darker than 53A; throat, close to 31A; at the base of the throat, close to 145A. Petal, fully opened, lower surface: Close to 47A; tube, close to 53C; at the base of the tube, close to 145A.

*Corona*.—Quantity and arrangement: Five sepals arranged in a single whorl. Sepal length: About 8 mm.

Sepal width: About 3 mm. Sepal shape: Ovate. Sepal apex: Narrowly acuminate. Sepal base: Roughly truncate. Sepal margin: Entire. Sepal texture, upper and lower surfaces: Smooth, glabrous. Sepal color: Immature, upper and lower surfaces: Close to 145B. Mature, upper and lower surfaces: Close to 145A; apex, close to 46A.

*Peduncles*.—Length: About 15.9 cm. Diameter: About 3 mm. Texture: Smooth, glabrous. Strength: Flexible, but strong. Color: Close to 143A.

*Pedicels*.—Length: About 2.4 cm. Diameter: About 3 mm. Texture: Smooth, glabrous. Strength: Flexible, but strong. Color: Close to 144C.

*Reproductive organs*.—Stamens: Quantity and arrangement: Typically five; basifixed; anthers connivent. Filament length: About 1 mm. Anther shape: Narrowly oblong. Anther length: About 9 mm. Anther color: Close to 160A. Pollen amount: None observed. Pistils: Quantity: Typically one. Pistil length: About 1.2 cm. Style length: About 1 cm. Style color: Close to 145D. Stigma shape: Sagittate. Stigma color: Close to 144C. Ovary color: Close to 144B.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be hardy to USDA Hardiness Zone 9.

It is claimed:

1. A new and distinct *Mandevilla* plant named 'Lanlouisiana' as illustrated and described.

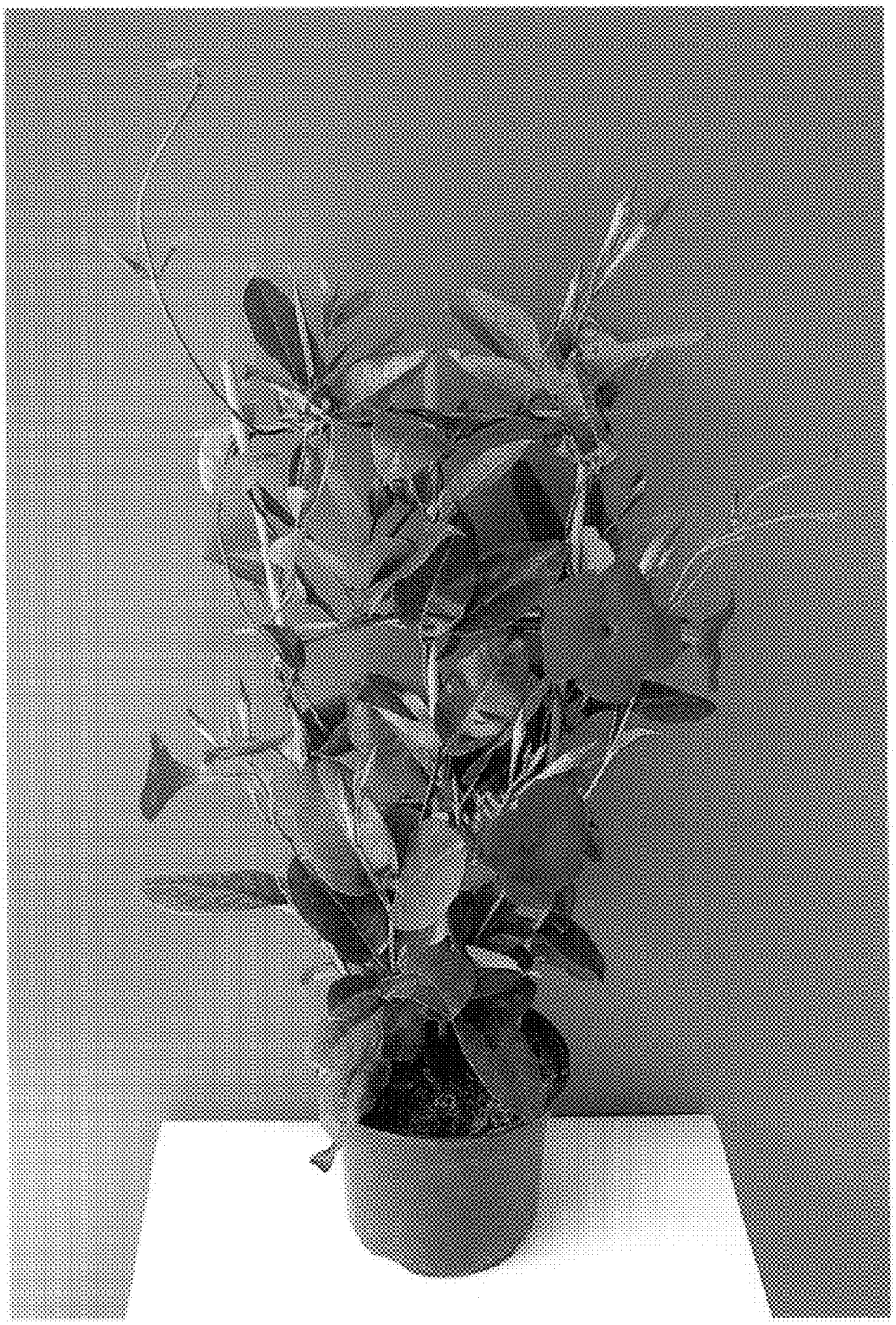

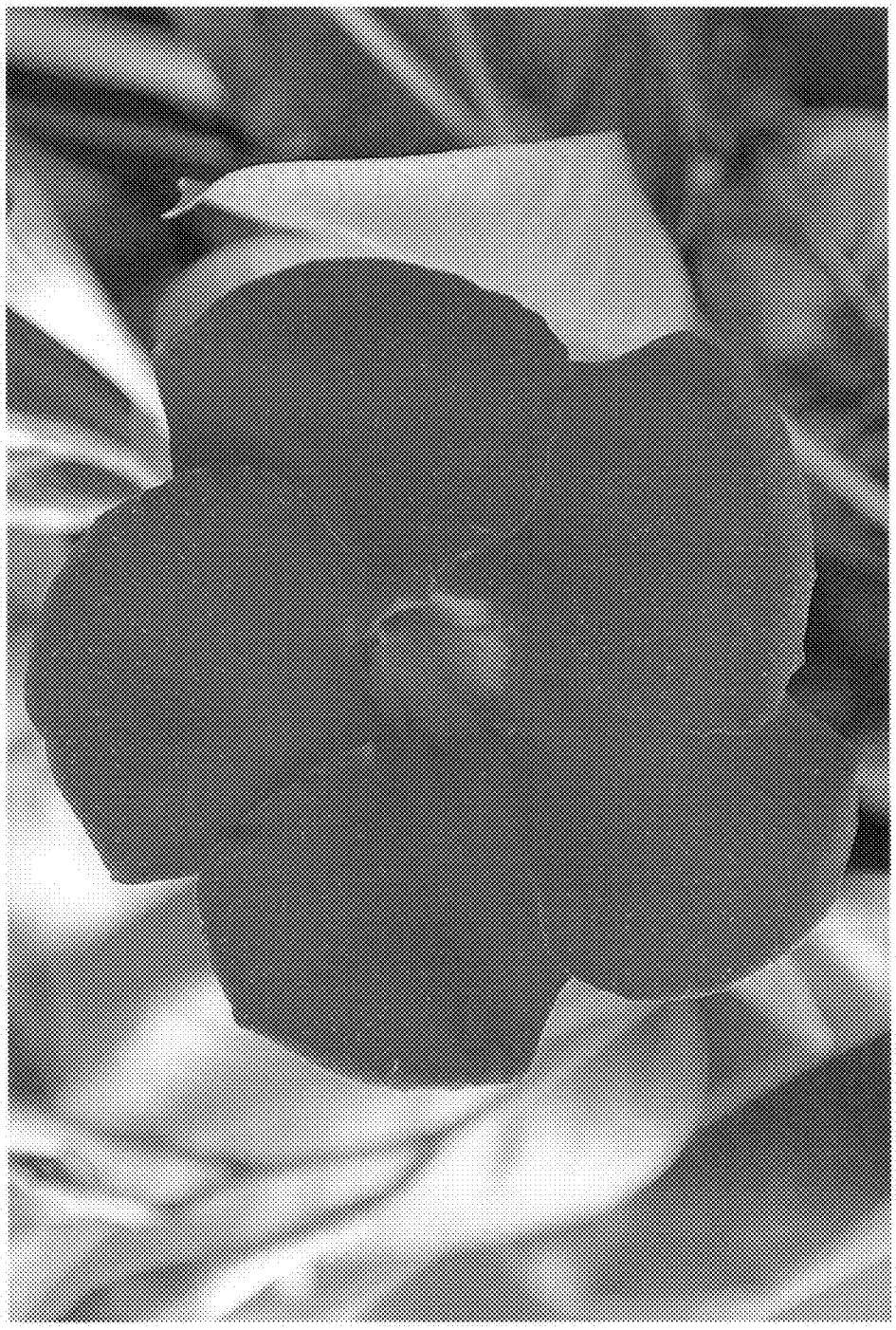

* * * * *